United States Patent [19]

Laurenzo

[11] Patent Number: 5,177,250

[45] Date of Patent: Jan. 5, 1993

[54] HYDROGENATION OF AROMATIC-SUBSTITUTED OLEFINS USING ORGANORUTHENIUM CATALYST

[75] Inventor: Kathleen S. Laurenzo, Baton Rouge, La.

[73] Assignee: Ethyl Corporation, Richmond, Va.

[21] Appl. No.: 698,822

[22] Filed: May 13, 1991

[51] Int. Cl.$^5$ .............................................. C07C 69/76
[52] U.S. Cl. ................................... 560/100; 560/103; 560/52; 560/56; 560/55; 564/180; 564/182; 564/300; 558/388
[58] Field of Search ...................... 560/52, 56, 55, 100, 560/103; 564/180, 182, 300; 558/388

[56] References Cited

PUBLICATIONS

Ohkuma, T. et al., Tetrahedron Lett., 31(38) 5509-12 1990.
CA 110(26):233528h 1989.
Takaya, H. et al. JACS 109(5) 1596-7 1987.
Lubell, W. et al. Tetrahedron 2(7) 543-54 1991.

*Primary Examiner*—Paul J. Killos
*Attorney, Agent, or Firm*—Richard J. Hammond

[57] ABSTRACT

A process is disclosed for the enantioselective hydrogenation of olefins of the formula

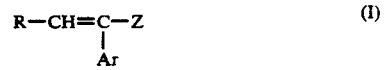

where R is hydrogen or $C_1$ to $C_6$ linear or branched alkyl, Z is

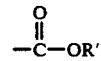

where R' is hydrogen or $C_1$ to $C_6$ linear or branched alkyl, —CN, C(NH)OR" where R" is $C_1$ to $C_6$ linear or branched alkyl, or —C(O)NH$_2$; and Ar is phenyl or naphthyl unsubstituted or substituted with benzoyl or substituted benzoyl, $C_1$ to $C_6$ linear or branched alkyl, $C_1$ to $C_6$ linear or branched alkoxy, halo, or carboxylic acid or $C_1$ to $C_6$ linear or branched alkyl ester thereof, which comprises contacting said aromatic-substituted olefin with a catalytically effective amount of a ruthenium phosphite complex.

15 Claims, No Drawings

HYDROGENATION OF AROMATIC-SUBSTITUTED OLEFINS USING ORGANORUTHENIUM CATALYST

FIELD OF THE INVENTION

This invention relates to a process for the catalytic reduction of aromatic-substituted olefins. More specifically, this invention relates to a process for asymmetrically, catalytically reducing aromatic-substituted olefins using organo ruthenium phosphines.

BACKGROUND OF THE INVENTION

Enantioselective catalysis using chiral metal complexes provides one of the most general and flexible methods for achieving asymmetric organic reactions. Metallic elements possess a variety of catalytic activities, and permutations of organic ligands or other auxiliary groups directing the steric course of the reaction are practically unlimited. Efficient ligands must be endowed with, for example, suitable functionality, an appropriate element of symmetry, substituents capable of differentiating space either electronically or sterically and skeletal rigidity or flexibility.

Among the asymmetric organic reactions catalyzed by chiral transition metal complexes, asymmetric hydrogenation has been one of the best studied, due in large part to the fact that it is the basis for the first commercialized catalytic asymmetric process. See, for example, ApSimon, et al., Tetrahedron, 1986, 42, 5157.

Some of the more interesting of the asymmetric hydrogenation catalysts are those derived from BINAP [2,2'-bis(diphenylphosphino)-1,1'-binaphthyl]. See, for example, U.S. Pat. Nos.: 4,691,037; 4,739,084; 4,739,085; and 4,766,227. Unlike the more classical models of chiral (asymmetric) molecules, chirality in the case of the BINAP compounds arises from the restricted rotation about the single bond joining the naphthalene rings. Because of such restricted rotation, perpendicular disymmetric planes result. Isomers arising from this type of asymmetry are termed atropisomers.

Cationic rhodium-BINAP complexes have been shown to catalyze the isomerization of allylamines to chiral enamines in 94–96% ee. Also, hydrogenations of geraniol and nerol (bis-unsaturated alcohols) using rhodium-BINAP complexes produce products in about 50% ee's. The synthesis of BINAP derivatives bearing groups other than phenyl on phosphorus such as paramethylphenyl and cyclohexyl have also been prepared. Inoue, et al., Chem. Lett., 1985, 1007.

Studies on the mechanism of rhodium-phosphine catalyzed asymmetric reductions of α,β-unsaturated acids or esters bearing an α-acetamido group have shown that the reaction proceeds by the displacement of solvent by the unsaturated substrate forming a chelate complex in which the olefin and the carbonyl oxygen of the acetamido function are bound to the metal. See Halpern, J., Asymmetric Synthesis, Vol. 5, pp. 41–69, J. D. Morrison, Ed., Academic Press, Inc., 1985. Substrates lacking the α-acetamido group are reduced with far less stereoselectivity. α, β and β,γ-unsaturated amides similarly form complexes in which the olefin and carboxamide oxygen are bound to rhodium. These reactions proceed with high stereoselectivity. See Brown, et al, J. Org. Chem., 47, 2722 (1982) and Koenig, K. E., Asymmetric Synthesis, Vol. 5, pp. 71–101, J. D. Morrison, Ed., Academic Press, Inc., 1985.

The BINAP ruthenium complexes are dramatically different than the rhodium ones. They have been used to catalyze a variety of asymmetric hydrogenations, including the hydrogenation of enamides and alkyl and aryl-substituted acrylic acids. See Noyori, et al., Modern Synthetic Methods, 1989, 5, 115, incorporated herein by reference.

However, unlike the rhodium catalyzed reductions, ruthenium (II) carboxylate complexes possessing the BINAP ligand are efficient catalysts for the enantioselective transformation of α,β-unsaturated carboxylic acids. Amide-bearing olefins as well as carboxylic acid esters are essentially unreactive with these catalysts. According to Ohta, et al, J. Org. Chem, 52, 3174 (1982), the carboxylate moiety, and not other oxygen containing groups, is responsible for the stereoselective reaction. Noncarboxylate-containing substrates ar unaffected by ruthenium complexes in these asymmetric reductions.

Accordingly, the prior art does not lead to the use of noncarboxylate-containing α,β-olefins as viable candidates for asymmetric reductions.

SUMMARY OF THE INVENTION

The present invention involves a novel method for the use of organo ruthenium-carboxylate catalysts which, when comprised of ligands having optical activity, can be used as the catalyst for effecting the asymmetric reduction of certain unsaturated organic compounds.

DESCRIPTION OF THE PREFERRED EMBODIMENTS

The process of the present invention involves the enantioselective hydrogenation (reduction) of aromatic-substituted olefins of the formula

where R is hydrogen or $C_1$ to $C_6$ linear or branched alkyl; Z is selected from the group

where R' and R" are the same or different and are $C_1$ to $C_6$ linear or branched alkyl; and Ar is phenyl or naphthyl unsubstituted or substituted with benzoyl or substituted benzoyl, $C_1$ to $C_6$ linear or branched alkyl, $C_1$ to $C_6$ linear or branched alkoxy, halo (chloro, bromo, iodo or fluoro), or carboxylic acid or the carboxylic acid alkyl esters thereof. The term "substituted" as used herein means a benzoyl group having at least one substituent such as halo, amino, nitro, hydroxy, $C_1$ to $C_6$ linear or branched alkyl or $C_1$ to $C_6$ linear or branched alkoxy.

In the above olefins, it is preferred that R is hydrogen, methyl or ethyl; R' and R" are the same and are methyl or ethyl; and Ar is phenyl or naphthyl unsubstituted or substituted with benzoyl, methyl, isobutyl, methoxy, chloro or fluoro. Most preferably R is hydrogen, R' and R" are the same and are methyl or ethyl and Ar is phenyl substituted with isobutyl or naphthyl substituted with methoxy.

None of the above compounds, including the preferred compounds as well as the most preferred compounds, are novel, their preparation being illustrated by the reaction schemes set out below:

1) for R—CH=C(Ar)—Z  where Z is —CN.

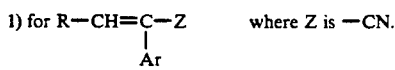

See Neway et al., J. Amer. Chem. Soc., 72 5645 (1950).

2) for RCH=C(Ar)—Z  where Z is —C(O)NH$_2$.

See U.S. Pat. Nos. 3,478,105, and 3,816,443.

3) for RCH=C(Ar)—Z  where Z is —C(O)OR".

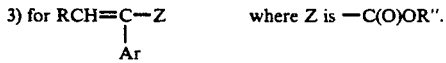

See Villieras et al., Synthesis, 1984, 406–8 and Seitz et al., West German Patent DE 3317356.

The asymmetric reduction process of the present invention employs a catalyst that, as noted herein, has been described as a ruthenium BINAP complex. It has the formula: $Ru_xH_yCl_z(R^4\text{-BINAP})_2(A)_p$ (II) where $R^4$-BINAP signifies a tertiary phosphine of the formula

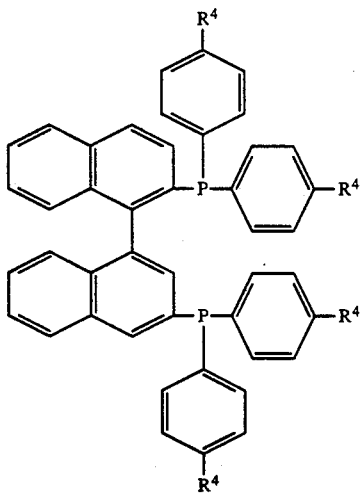

(III)

where $R^4$ is a hydrogen, methyl or methoxy group; A is a tertiary amine; when y is 0, then x is 2, z is 4 and p is 1; and when y is 1, then x is 1, z is 1 and p is 0, as well as those having the formula

$[Ru(X-R^5\text{-BINAP})_q OC\text{-}R^6]OCR^7$, where X-R$^5$-BINAP is

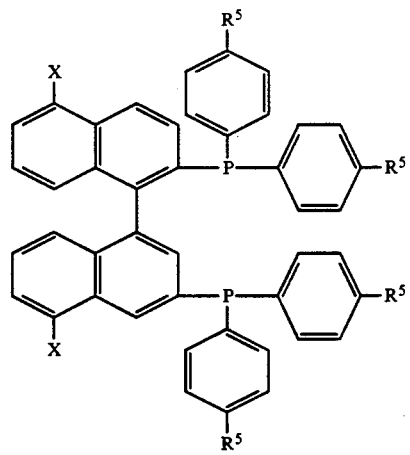

(IV)

wherein X represents a hydrogen atom, an amino group, an acetylamino group or a sulfo group; $R^5$ represents a hydrogen atom or alkyl group having from 1 to 9 carbon atoms, a halogenated alkyl group having from 1 to 4 carbon atoms (examples of the halogen include fluorine, chlorine and bromine), a phenyl group, a phenyl group substituted with an alkyl group having from 1 to 4 carbon atoms, and α-aminoalkyl group (e.g., those having from 1 to 4 carbon atoms), or an α-aminophenylalkyl group (e.g., those having from 7 to 10 carbon atoms), or $R^6$ to $R^7$ are taken together to form an alkylene group having from 1 to 4 carbon atoms; and q represents 1 or 2; or $[RuH_t(R^4BINAP)_v]Y_w$       (V)

where $R^4$BINAP is a tertiary phosphine of formula (IV); Y is $ClO_4$, $BF_4$ or $PF_6$; when t is 0, then v is 1 and w is 2; and when t is 1, then v is 2 and w is 1.

The ruthenium-optically active phosphine complex of formula (II) can be obtained by the methods referenced in Ohta, et al, ibid, or as further described in Ikariya, et al, J. Chem. Soc., Chem. Commun., pp. 922–924 (1985) as well as in European Patent No. 174,057A and European Patent Application No. 87310023.4, all of which are incorporated in their entirety by reference herein. Specific examples of the optically active ruthenium phosphine complex are:

Ru$_2$Cl$_4$(BINAP)$_2$(NEt$_3$);
R$_2$Cl$_4$(T-BINAP)$_2$(NEt$_3$);
RuHCl(BINAP)$_2$;
RuHCl(T-BINAP)$_2$;
Ru(BINAP)(O$_2$CCH$_3$)$_2$;
Ru(BINAP)(O$_2$CCF$_3$)$_2$;
Ru(BINAP)(O$_2$CPh)$_2$; and
Ru(sulfonated BINAP) (O$_2$CCH$_3$)$_2$.

As noted earlier, the above catalysts are useful in stereoselective hydrogenation of olefinic compounds of the formula

where R, Z and Ar are defined above. Solutions of these olefins are typically admixed with a catalytically effective amount of the ruthenium complexes and hydrogenated at about 20° C. to about 100° C. under about 20 to about 1000 psi of hydrogen.

EXAMPLES

The present invention is described in greater detail by reference to the following non-limiting Examples.

Methods (General):

All solvents used in the hydrogenation were reagent grade and were sparged with nitrogen for at least 2 hours to remove oxygen. The (1,5-cyclooctadiene) ruthenium (II) chloride polymer used was a commercially available material. Conversions were determined by gc (area %) using a 15 m×0.053 mm (1.2 mm film) SE-54 EconoCap column, 120°–250° C. at 10° C./min. after a 2 min. hold. Optical purities were determined by HPLC using a chiral AGP100-4 column (from advanced Separation Technologies) and as eluent 1% (V/V) isopropanol in water containing $KH_2PO_4$ and N,N-dimethyloctylamine. The metal reactors used were constructed of Hastelloy C, Monel 400 or 316 Stainless Steel.

Preparation of (S-BINAP) Ruthenium (II) Diacetate

The material was made by the method of T. Ohta, H. Takaya and R. Noyori, Inorg. Chem., 1988, 27, 566.

Hydrogenation Procedure

The reactor was charged in a dry-box as follows:

1 mmole substrate was dissolved in 30 ml methanol and 0.02 mmole (S-BINAP) ruthenium (II) diacetate was added. The reactor was closed, removed from the dry box and pressured to 1000 psig with $H_2$. The reaction mixture was stirred at ambient temperature for 20–24 hours.

Results:

| Substrate | Temp (°C.) | Time (hr.) | Conv. (%) | % ee |
|-----------|------------|------------|-----------|------|
| UAm       | 23         | 20         | 100       | 70   |
| UME       | 24         | 24         | 28        | 34   |

UAm is 2-[4'-isobutylphenyl]acrylamide.
UME is methyl 2-[4'-isobutylphenyl]acrylate.

What is claimed is:

1. A process for the enantioselective hydrogenation of an aromatic-substituted olefin of the formula

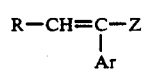
(I)

where R is hydrogen or $C_1$ to $C_6$ linear or branched alkyl, Z is

where R' is hydrogen or $C_1$ to $C_6$ linear or branched alkyl, —CN, C(NH)OR" where R" is $C_1$ to $C_6$ linear or branched alkyl, or —C(O)NH$_2$; and Ar is phenyl or naphthyl unsubstituted or substituted with benzoyl or substituted benzoyl, $C_1$ to $C_6$ linear or branched alkyl, $C_1$ to $C_6$ linear or branched alkoxy, halo, or carboxylic acid or $C_1$ to $C_6$ linear or branched alkyl ester thereof, which comprises contacting said aromatic-substituted olefin with a catalytically effective amount of a ruthenium phosphite complex of the formula $Ru_xH_yCl_z(R^4\text{-BINAP})_2(A)_p$, where $R^4$-BINAP is

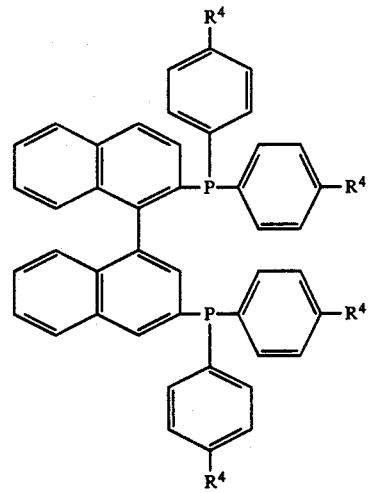
(III)

where $R^4$ is a hydrogen, methyl or methoxy group; A is a tertiary amine; when y is 0, then x is 2, z is 4 and p is 1; and when y is 1, then x is 1, z is 1 and p is 0.

2. The process according to claim 1 where R is hydrogen or methyl or ethyl, R' and R" are the same and are methyl or ethyl and Ar is phenyl or naphthyl unsubstituted or substituted with benzoyl, methyl, isobutyl, methoxy, chloro or fluoro.

3. The process according to claim 2 where R' and R" are the same and are methyl or ethyl and Ar is phenyl substituted with isobutyl or naphthyl substituted with methoxy.

4. The process according to claim 3 where R is hydrogen.

5. The process according to claim 4 where Z is

6. A process for the enantioselective hydrogenation of an aromatic-substituted olefin of the formula

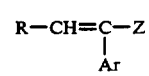
(I)

where R is hydrogen or $C_1$ to $C_6$ linear or branched alkyl, Z is

where R' is hydrogen or $C_1$ to $C_6$ linear or branched alkyl, —CN, C(NH)OR" where R" is $C_1$ to $C_6$ linear or branched alkyl, or —C(O)NH$_2$; and Ar is phenyl or naphthyl unsubstituted or substituted with benzoyl or substituted benzoyl, $C_1$ to $C_6$ linear or branched alkyl, $C_1$ to $C_6$ linear or branched alkoxy, halo, or carboxylic acid or $C_1$ to $C_6$ linear or branched alkyl ester thereof, which comprises contacting said aromatic-substituted olefin with a catalytically effective amount of a ruthenium phosphite complex of the formula

where X-R⁵-BINAP is

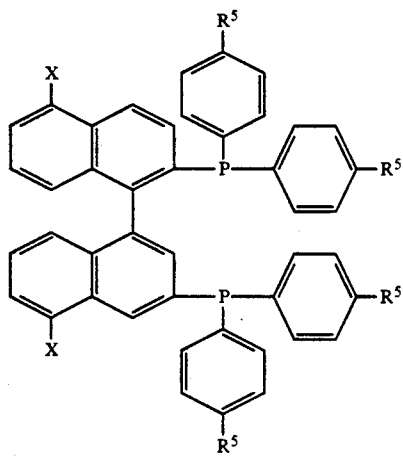
(IV)

wherein X represents a hydrogen atom, an amino group, an acetylamino group or a sulfo group; $R^5$ represents a hydrogen atom or alkyl group having from 1 to 9 carbon atoms, a halogenated alkyl group having from 1 to 4 carbon atoms (examples of the halogen include fluorine, chlorine and bromine), a phenyl group, a phenyl group substituted with an alkyl group having from 1 to 4 carbon atoms, and α-aminoalkyl group (e.g., those having from 1 to 4 carbon atoms), or an α-aminophenylalkyl group (e.g., those having from 7 to 10 carbon atoms), or $R^6$ and $R^7$ are taken together to form an alkylene group having from 1 to 4 carbon atoms; and q represents 1 or 2.

7. The process according to claim 6 where R is hydrogen or methyl or ethyl, R' and R" are the same and are methyl or ethyl and Ar is phenyl or naphthyl unsubstituted or substituted with benzoyl, methyl, isobutyl, methoxy, chloro or fluoro.

8. The process according to claim 7 where R' and R" are the same and are methyl or ethyl and Ar is phenyl substituted with isobutyl or naphthyl substituted with methoxy.

9. The process according to claim 8 where R is hydrogen.

10. The process according to claim 9 where Z is

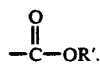

11. A process for the enantioselective hydrogenation of an aromatic-substituted olefin of the formula R—CH=C—Z (I)
        |
        Ar where R is hydrogen or $C_1$ to $C_6$ linear or branched alkyl, Z is

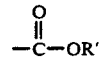

where R' is hydrogen or $C_1$ to $C_6$ linear or branched alkyl, —CN, C(NH)OR" where R" is $C_1$ to $C_6$ linear or branched alkyl, or —C(O)NH₂; and Ar is phenyl or naphthyl unsubstituted or substituted with benzoyl or substituted benzoyl, $C_1$ to $C_6$ linear or branched alkyl, $C_1$ to $C_6$ linear or branched alkoxy, halo, or carboxylic acid or $C_1$ to $C_6$ linear or branched alkyl ester thereof, which comprises contacting said aromatic-substituted olefin with a catalytically effective amount of a ruthenium phosphite complex of the formula $[RuH_t(R^4BINAP)_v]Y_w$ (V)

where R⁴BINAP is a tertiary phosphine of formula $[Ru(X-R^5-BINAP)_qOC-R^6]OCR^7$ where X-R⁵-BINAP is

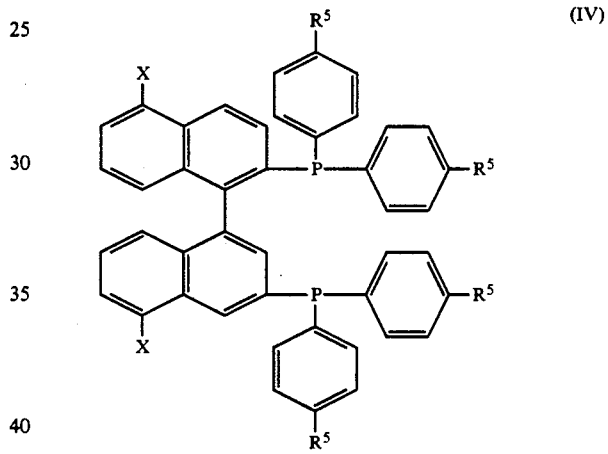
(IV)

wherein X represents a hydrogen atom, an amino group, an acetylamino group or a sulfo group; $R^5$ represents a hydrogen atom or alkyl group having from 1 to 9 carbon atoms, a halogenated alkyl group having from 1 to 4 carbon atoms, a phenyl group, a phenyl group substituted with an alkyl group having from 1 to 4 carbon atoms, and α-aminoalkyl group; Y is ClO₄, BF₄, or PF₆; when t is 0, then v is 1 and w is 2; and when t is 1, than v is 2 and w is 1.

12. The process according to claim 11 where R is hydrogen or methyl or ethyl, R' and R" are the same and are methyl or ethyl and Ar is phenyl or naphthyl unsubstituted or substituted with benzoyl, methyl, isobutyl, methoxy, chloro or fluoro.

13. The process according to claim 12 where R' and R" are the same and are methyl or ethyl and Ar is phenyl substituted with isobutyl or naphthyl substituted with methoxy.

14. The process according to claim 13 where R is hydrogen.

15. The process according to claim 14 where Z is

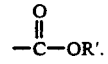

* * * * *